US010420340B2

(12) United States Patent
Knight et al.

(10) Patent No.: US 10,420,340 B2
(45) Date of Patent: Sep. 24, 2019

(54) AGROCHEMICAL CONCENTRATES

(71) Applicant: CRODA INTERNATIONAL PLC, Goole Yorkshire (GB)

(72) Inventors: Kathryn Marie Knight, Yorkshire (GB); James Alexander Flavell, Yorkshire (GB)

(73) Assignee: CRODA INTERNATIONAL PLC, East Yorkshire (GB)

( * ) Notice: Subject to any disclaimer, the term of this patent is extended or adjusted under 35 U.S.C. 154(b) by 0 days.

(21) Appl. No.: 15/037,504

(22) PCT Filed: Nov. 19, 2014

(86) PCT No.: PCT/GB2014/053417
§ 371 (c)(1),
(2) Date: May 18, 2016

(87) PCT Pub. No.: WO2015/075443
PCT Pub. Date: May 28, 2015

(65) Prior Publication Data
US 2016/0278371 A1     Sep. 29, 2016

(30) Foreign Application Priority Data
Nov. 22, 2013  (GB) .................................. 1320627.1

(51) Int. Cl.
| *A01N 25/30* | (2006.01) |
| *A01N 25/04* | (2006.01) |
| *A01N 25/08* | (2006.01) |
| *A01N 41/10* | (2006.01) |

(52) U.S. Cl.
CPC ............ *A01N 25/30* (2013.01); *A01N 25/04* (2013.01); *A01N 25/08* (2013.01); *A01N 41/10* (2013.01)

(58) Field of Classification Search
None
See application file for complete search history.

(56) References Cited

U.S. PATENT DOCUMENTS

| 3,637,357 | A | 1/1972 | Nixon |
| 5,872,149 | A | 2/1999 | Dralle-Voss |
| 7,521,397 | B2 | 4/2009 | Dunkel |
| 2004/0082481 | A1* | 4/2004 | Griffiths ................. A01N 25/04 504/361 |
| 2004/0157745 | A1 | 8/2004 | Vermeer |
| 2004/0176480 | A1 | 9/2004 | Dyllick-Brenzinger et al. |
| 2005/0037926 | A1 | 2/2005 | Zerrer |
| 2012/0309626 | A1 | 12/2012 | Turk |
| 2014/0206541 | A1* | 7/2014 | Oester .................... A01N 25/30 504/195 |

FOREIGN PATENT DOCUMENTS

| CN | 102986658 | 3/2013 |
| CN | 1029896718 | 3/2013 |
| EP | 0161595 | 11/1985 |
| EP | 1671617 | 6/2006 |
| JP | 5612340 | 2/1981 |
| JP | 06329168 | 11/1994 |
| JP | 10025224 | 1/1998 |
| JP | 11209231 | 8/1999 |
| WO | 03070705 | 8/2003 |
| WO | 2004011542 | 2/2004 |
| WO | 2004016088 | 2/2004 |
| WO | 2006043048 | 4/2006 |
| WO | 2007074331 | 7/2007 |
| WO | 2008059234 | 5/2008 |
| WO | 03000055 | 2/2010 |
| WO | 2010017651 | 2/2010 |
| WO | 2011073220 | 8/2011 |
| WO | 2012167321 | 12/2012 |
| WO | 2015023426 A1 | 2/2015 |
| WO | 2015023434 A1 | 2/2015 |
| WO | 2015040362 A1 | 3/2015 |
| WO | 2015044639 A1 | 4/2015 |

OTHER PUBLICATIONS

International Search Report dated Feb. 3, 2015 for international Application No. PCT/GB2014/053417, 7 pages.
International Preliminary Report on Patentability and Written Opinion of the International Searching Authority for International Application No. PCT/GB2014/053417, dated May 24, 2016, 7 pages.
Database WPI, Week 197834, Thomson Scientific, London GB; AN 1978-61210A, XP002734601, Jul. 19, 1978, 2 pages.
Database WPI, Week 198301, Thomson Scientific, London GB; AN 1983-01072K, XP002734603, Nov. 19, 1982, 2 pages.
Russian Office Action for Russian Application No. 2016124569/13(038575), dated Jan. 25, 2018, including English translation, 12 pages.
European Communication for European Application No. 14 806 352.2-1110, dated Apr. 18, 2018, 4 pages.

* cited by examiner

*Primary Examiner* — Alton N Pryor
(74) *Attorney, Agent, or Firm* — RatnerPrestia

(57) ABSTRACT

An agrochemical formulation comprising a structurant, surfactant adjuvant, and optionally an agrochemical active and/or nutrient. The structurant is a polyol ester of a $C_4$ to $C_{16}$ dicarboxylic acid, and may be obtainable by the reaction of $C_4$ to $C_{16}$ dicarboxylic acid, $C_2$ to $C_8$ polyol, and $C_{16}$ to $C_{30}$ monocarboxylic fatty acid. There is also provided a method of making the concentrate. The structurant is suitable for use in concentrates and agrochemical formulations to provide structuring in adjuvant based systems.

25 Claims, No Drawings

AGROCHEMICAL CONCENTRATES

CROSS REFERENCE TO RELATED APPLICATIONS

This application is the National Stage filing of International Appln. No. PCT/GB2014/053417, filed 19 Nov. 2014, and claims priority of GB Application No. 1320627.1, filed 22 Nov. 2013, the entirety of which applications is incorporated herein by reference for all purposes.

FIELD OF THE INVENTION

The present invention relates to structurants for agrochemical active formulations, and in particular for use in said formulations for suspending solids in suspension concentrate type formulations comprising one or more agrochemical actives and/or nutrients. The present invention also includes methods of treating crops with such formulations.

BACKGROUND OF THE INVENTION

Agrochemical formulations are commonly supplied to the end user as a concentrate which is then diluted for use. Adjuvant and agrochemical actives can be added in the tank mix at the point of dilution. However, preferably the adjuvants and actives are included in the concentrate. When the agrochemical active ingredient is insoluble or only partly soluble in water, the concentrate comprising the active is conveniently supplied in the form of a suspension concentrate (SC) in which finely divided solid particles of agrochemical are suspended in an aqueous formulation. Wetting agents and dispersants may also be including in the SC to wet and stabilise the solid particles. SC formulations may therefore typically comprise a solid active, surfactant, density/viscosity modifier system, freeze/thaw additive, bactericide, anti-foamer, and water diluent.

It is important that the solid particles remain suspended in the concentrate formulation without significant separation over an extended period of time under typical storage conditions. It is also important to prevent the dispersed solid particles in the SC from forming a hard pack sediment upon storage. It is therefore normally necessary to incorporate suspending or structuring agents in to the suspension concentrate. For example, existing structuring agents used for water-based SCs include polysaccharide gums, clays, celluloses, polyacrylates, and xantham gum.

The presence of high loadings of adjuvant in an SC formulation with consequent reduction in water content (both of which are highly desirable from efficacy and efficiency perspectives) present the formulator with major problems. Existing structuring agents are limited to the need for water in order to swell properly and provide adequate thickening to support a typical SC. The higher the amount of adjuvant that is included, in order to provide desired bioperformance, the more difficult it becomes to achieve a stable suspension concentrate. This problem is noted in US 2004/0082481.

SUMMARY OF THE INVENTION

Therefore, there is a need for structurants for agrochemical applications which are able to structure low aqueous and substantially non-aqueous concentrates. Additionally, there is a need for structurants which are able to suspend solid particles in a non-aqueous surfactant adjuvant without negatively impacting the finished product viscosity, and which are able to maintain solid active ingredient in suspension for a period of time to allow for storage without breakdown of the suspension.

The present invention also seeks to provide the use of structurants in agrochemical concentrate compositions in combination with an agrochemical active, where the structurant may provide comparable or improved properties compared to existing structurants.

The present invention also seeks to provide the use of agrochemical concentrates and dilute formulations thereof comprising said structurants.

DETAILED DESCRIPTION OF THE INVENTION

According to a first aspect of the present invention there is provided an agrochemical concentrate comprising;
  i) at least one structurant, said structurant being a polyol ester of a $C_4$ to $C_{16}$ dicarboxylic acid;
  ii) surfactant adjuvant; and
  iii) at least one agrochemical active and/or nutrient.

According to a second aspect of the present invention there is provided an agrochemical concentrate comprising;
  i) at least one structurant, said structurant being a polyol ester of a $C_4$ to $C_{16}$ dicarboxylic acid; and
  ii) surfactant adjuvant, wherein the amount of surfactant adjuvant present in the concentrate is at least 50 wt. %.

According to a third aspect of the present invention there is provided a method of preparing a concentrate according to the first aspect, said method comprising mixing;
  at least one agrochemical active and/or nutrient;
  at least one structurant, said structurant being a polyol ester of a $C_4$ to $C_{16}$ dicarboxylic acid; and
  surfactant adjuvant;
and grinding and/or milling said mixture.

According to a fourth aspect of the present invention there is provided an agrochemical formulation formed by dilution of the concentrate according to the first aspect or the second aspect.

According to a fifth aspect of the present invention there is provided the use of a polyol ester of a $C_4$ to $C_{16}$ dicarboxylic acid as a structurant in an agrochemical concentrate comprising surfactant adjuvant and at least one agrochemical active and/or nutrient.

According to a sixth aspect of the present invention there is provided a method of treating vegetation to control pests, the method comprising applying an agrochemical formulation of the fourth aspect, either to said vegetation or to the immediate environment of said vegetation.

It has been found that polyol esters of a $C_4$ to $C_{16}$ dicarboxylic acids provides for structurants having good adjuvant structuring properties, and which can allow for suspension concentrates with low or no water content therefore providing for high adjuvant loading.

As used herein, the terms 'for example,' 'for instance,' 'such as,' or 'including' are meant to introduce examples that further clarify more general subject matter. Unless otherwise specified, these examples are provided only as an aid for understanding the applications illustrated in the present disclosure, and are not meant to be limiting in any fashion.

It will be understood that, when describing the number of carbon atoms in a substituent group (e.g. '$C_1$ to $C_6$ alkyl'), the number refers to the total number of carbon atoms present in the substituent group, including any present in any branched groups. Additionally, when describing the number of carbon atoms in, for example fatty acids, this refers to the total number of carbon atoms including the one at the carboxylic acid, and any present in any branch groups.

The structurant is a polyol ester of a $C_4$ to $C_{16}$ dicarboxylic acid. The structurant of the present invention may be obtainable by the reaction of;
- $C_4$ to $C_{16}$ dicarboxylic acid;
- $C_2$ to $C_8$ polyol; and
- $C_{16}$ to $C_{30}$ monocarboxylic fatty acid.

The present invention is based on our finding that ester products obtainable by reaction of polyols, $C_4$ to $C_{16}$ dicarboxylic acids, and long chain monocarboxylic fatty acids, and in particular such structurants that have multiple pendent fatty acid groups usually also with free polyol hydroxyl groups, can be very effective structurants in adjuvant based systems.

In referring to compounds of and used in this invention as 'polyesters' or 'oligoesters', we are referring to the multiple ester linkages in the compounds—derived from reaction between the polyol and the di- and mono-carboxylic acids. They do not necessarily imply that the compounds have polyester chains—of alternating dicarboxylic acid and polyol, although such chains are a desirable feature of many compounds of and used in the invention.

The term 'structurant' refers to the provision of effects ranging from increasing the viscosity (viscosifying or thickening) to gelling a continuous phase (creating a three dimensional structure at the molecular level which 'traps' the continuous phase) and includes the possibility of generating liquid crystal like phases in the continuous phase, all of which can enhance the stability of dispersed phases in the continuous phase.

The $C_2$ to $C_8$ polyol, typically used as a starting material in making the polyesters of the invention, may comprise in the range from 2 to 8 hydroxyl groups. Preferably, in the range from 3 to 7. Most preferably, in the range from 3 to 6. Especially preferred are where the number of hydroxyl groups is 3, 4, or 6.

The esterification with fatty acid and diacid will replace some or all of the hydrogen atoms (dependant on the molar ratio of the polyol group to alkoxylation group in the reaction) of the hydroxyl groups.

The $C_2$ to $C_8$ polyol may comprise in the range from 1 to 4 primary hydroxyl groups. Preferably, in the range from 1 to 3 primary hydroxyl groups. Most preferably, in the range from 1 to 2 primary hydroxyl groups (on the polyol terminal carbon atoms).

The $C_2$ to $C_8$ polyol may comprise in the range from 1 to 7 secondary hydroxyl groups. Preferably, in the range from 1 to 6 secondary hydroxyl groups. More preferably, in the range from 2 to 5 secondary hydroxyl groups. Most preferably, in the range from 3 to 5 secondary hydroxyl groups.

Preferably the polyol is a $C_3$ to $C_8$ polyol. More preferably, a $C_4$ to $C_7$ polyol, particularly a $C_3$ to $C_6$ polyol. Especially preferred are $C_3$, $C_5$, and $C_6$ polyols.

The polyol may be linear, branched, partially cyclic, or cyclic. Preferably, the polyol is linear or branched. More preferably, the polyol is linear.

The polyol may be selected from diols, triols, tetrols, pentols, hexols, heptols, or octols. Preferably, the polyol may be selected from triols, tetrols, pentols, hexols, or heptols. More preferably, the polyol may be selected from triols, tetrols, or hexols.

Suitable specific polyols may be selected from ethylene glycol, isosorbide, 1,3-propanediol, trimethylolpropane, glycerol, erythritol, threitol, pentaerythritol, sorbitan, arabitol, xylitol, ribitol, fucitol, mannitol, sorbitol, galactitol, iditol, inositol, or volemitol.

In one particular embodiment, polyols obtainable from natural sources may be preferred. In particular, sugar alcohols may be used as the polyol. In this specification the terms 'sugars' and 'sugar alcohols' refer to a group of saccharide derived polyols having from 4 to 8 hydroxyl groups. Examples of preferred sugars and sugar alcohols may include monosaccharides and disaccharides having from 4 to 8 hydroxyl groups. Monosaccharide, more preferably of glucose, fructose or sorbitol, and particularly of sorbitol or sorbitan, may be preferred as polyols obtained from natural sources.

Particularly preferred polyols are $C_5$ to $C_6$ polyols having 3, 4, or 6 hydroxyl groups. Further preferably, the polyol is glycerol, trimethylolpropane, sorbitol, sorbitan, or mixtures thereof. Most preferably, sorbitol or sorbitan.

The polyol may be homogeneous in that it comprises only one specific polyol. In an alternative embodiment, the polyol starting material used to form the structurant may be heterogeneous in that it comprises a mixture of a number of different polyols from those listed above, and therefore the polyol formed therefrom may be heterogeneous.

Where the polyol has four or more carbon atoms and four or more hydroxyl groups, usually two primary hydroxyls and two or more secondary hydroxyls, it may be susceptible to react by an intra-molecular etherification (anhydridisation) reaction to form cyclic ethers. For example sorbitol may form sorbitan cyclic ethers which may react further to form the dicyclic diether iso-sorbide, reducing the number of hydroxyl groups available for esterification. When sorbitan residues are desired in the product, it will usually be done by, in effect, in situ formation of the sorbitan; and correspondingly it is likely that some sorbitol will be converted into sorbitan when trying to make sorbitol esters.

Although anhydridisation may occur its extent may be controlled (at least to a limited extent) by selection of the reaction conditions e.g. use of acidic catalysts, particularly if linked with higher reaction temperatures, will lead to a greater degree of anhydridisation than the use of alkaline catalysts (and lower reaction temperatures will lead to a lower degree of anhydridisation).

The structurant is formed from a $C_4$ to $C_{16}$ dicarboxylic acid, i.e. having 4 to 16 carbon atoms.

The $C_4$ to $C_{16}$ dicarboxylic acid may be aliphatic or aromatic. Said acids may be linear dicarboxylic acids, in that they comprise terminal carboxyl groups, wherein the terminal carboxyl groups are bridged by a $C_6$ to $C_{14}$ alkyl group, or a $C_6$ to $C_{14}$ alkenyl group.

The term '$C_6$ to $C_{14}$ alkyl' as used herein, unless otherwise defined, refers to saturated hydrocarbon radicals being straight chain, branched, or cyclic moieties, containing from 6 to 14 carbon atoms.

The term '$C_6$ to $C_{14}$ alkenyl' as used herein, unless otherwise defined, refers to hydrocarbon radicals having in the range from 6 to 14 carbon atoms, and comprising at least one carbon-carbon double bonds. The alkenyl radicals may be straight chain or branched.

Preferably, the $C_4$ to $C_{16}$ dicarboxylic acid is linear and has a $C_6$ to $C_{14}$ alkyl bridging group.

In one embodiment, said $C_4$ to $C_{16}$ dicarboxylic acid may be selected from a linear aliphatic dicarboxylic acid comprising in the range from 4 to 16 carbon atoms.

Preferably, in the range from 6 to 14 carbon atoms. More preferably, in the range from 8 to 12 carbon atoms.

In this embodiment, preferred examples of $C_4$ to $C_{16}$ dicarboxylic acid may be independently selected from adipic acid (hexanedioic acid), pimelic acid (heptanedioic acid), suberic acid, azelaic acid, sebacic acid (decanedioic acid), undecane dicarboxylic acid, dodecane dicarboxylic acid (dodecanedioic acid), tetradecanedioic acid, hexadecanedioic acid, or combinations thereof. More preferably, said acid is selected from suberic acid, sebacic acid, or dodecanedioic acid. Most preferably, sebacic acid.

Alternatively, said acids may comprise terminal carboxyl groups bridged by at least one cyclic group. The cyclic groups may be saturated or unsaturated cyclic groups, and selected from $C_5$ or $C_6$ cycloalkyls, $C_6$ cycloaryl, or 4 to 7 membered heterocyclics.

The term 'cycloalkyl' as used herein, unless otherwise defined, refers to an organic radical derived from a saturated hydrocarbon, and may be selected from cyclopentane or cyclohexane. The term 'cycloaryl' as used herein, unless otherwise defined, refers to an organic radical derived from an aromatic hydrocarbon by removal of one hydrogen, and may be phenyl.

The term 'heterocylic' as used herein, unless otherwise defined, refers to monocyclic radicals comprising 4 to 7 membered ring systems, in which the ring contains at least one or more heteroatom selected from nitrogen or oxygen. The ring may be non-aromatic, partly aromatic, wholly aromatic, or contain one or more non-conjugated double bonds. Examples of heterocyclic radicals may be independently selected from pyrrolidinyl, imidazolyl, indolyl, furanyl, or oxazolyl. Preferably, the heterocyclic radical is furanyl.

In the embodiment where the terminal carboxyl groups are bridged by at least one cyclic group, suitable examples of dicarboxylic acids may be selected from terephthalic acid, (ortho) phthalic acid, isopthalic acid, or 2,5-furandicarboxylic acid, The monocarboxylic fatty acids used in forming the structurant of the present invention are selected from $C_{16}$ to $C_{30}$ fatty acids, more preferably $C_{16}$ to $C_{28}$ fatty acids, particularly $C_{18}$ to $C_{26}$ fatty acids. Especially $C_{20}$ and $C_{24}$ fatty acids may be preferred.

The fatty acids may be selected from linear or branched fatty acids. The fatty acids may be selected from saturated or unsaturated fatty acids. Preferably, the fatty acids are selected from saturated linear fatty acids.

Suitable saturated fatty acids may be selected from palmitic acid, stearic acid, arachidic acid, behenic acid, lignoceric acid, cerotic acid, or montanic acid. Preferred saturated fatty acids may be selected from palmitic acid, stearic acid, arachidic acid, behenic acid, lignoceric acid, or cerotic acid. Most preferably, arachidic acid, behenic acid, or lignoceric acid.

Where unsaturated fatty acids are present, these may be selected from unsaturated fatty acids comprising at least one unsaturated carbon-carbon double bond. Particularly preferred are unsaturated fatty acids having in the range from 1 to 3 carbon-carbon double bonds. Most preferred are mono-unsaturated or di-unsaturated fatty acids residues. The carbon-carbon double bond(s) of the fatty chain may be present either in a cis or a trans configuration.

Preferably, said unsaturated fatty acid is linear and mono-unsaturated.

Iodine values are understood to represent the average amount of unsaturation of fats or oils, and is expressed in terms of the number of centigrams of iodine absorbed per gram of sample (% iodine absorbed). Where unsaturated fatty acids are present, said fatty acids may be selected such that the iodine value is greater than 70. Preferably, said iodine value is greater than 75. More preferably, said iodine value is greater than 80. Most preferably, said iodine value is greater than 85.

Suitable unsaturated fatty acids may be selected from myristoleic acid, palmitoleic acid, sapienic acid, oleic acid, elaidic acid, vaccenic acid, linoleic acid, linoelaidic acid, arachidonic acid, eicosapentaenoic acid, erucic acid, or docosahexaenoic acid. Preferred unsaturated fatty acids may be selected from arachidonic acid, eicosapentaenoic acid, erucic acid, or docosahexaenoic acid. Most preferably, erucic acid.

Preferably, said unsaturated fatty acid is linear and mono-unsaturated.

The fatty acids may be obtained from natural fats and oils, and these may be selected from canola oil, sunflower oil, soybean oil, olive oil, cotton seed oil, grape seed oil, peanut oil, rapeseed oil, safflower oil, cottonseed oil, or tall oil. Preferably, canola oil, safflower oil, soybean oil, or tall oil.

In an alternative embodiment, the fatty acid used may be purified prior to use in the present invention. Purification may be undertaken to raise the levels of desired fatty acid chains and reduce the level of undesired fatty acid.

Mixtures of monocarboxylic acids may be used if desired and it may be advantageous in permitting the properties of the products to be adjusted. Using combinations of long chain monocarboxylic acids will generally give products whose properties are intermediate between the properties of the respective products made wholly with the respective fatty acids. Including small proportions of short chain (particularly shorter than 16 carbon atoms) or branched or unsaturated monocarboxylic acids (of any chain length) will tend to make the products less likely to be gellant type structurants. The proportions of short chain or branched or unsaturated monocarboxylic acids, if present, will generally be low, typically an average of not more than 30 mol. %, more usually not more than 25 mol. %, and desirably not more than 20 mol. % e.g. from 1 to 20 mol. %, and particularly from 5 to 15 mol. % of the total moncarboxylic fatty acid residues in the compounds.

The molar ratio of $C_4$ to $C_{16}$ dicarboxylic acid, $C_2$ to $C_8$ polyol, and $C_{16}$ to $C_{30}$ monocarboxylic fatty acid present in the structurant is preferably in the range from 0.5-1.5:1.5-2.5:2.5-3.5 respectively. Preferably, in the range from 0.8-1.2:1.8-2.2:2.8-3.2 respectively. Most preferably, about 1:2:3 respectively.

The molecular weight (number average) of the structurant is preferably in the range from 600 to 8,000, more preferably 800 to 2,000, most preferably 1,100 to 1,700. The molecular weight (weight average) of the structurant is preferably in the range from 1,500 to 12,000, more preferably 2,000 to 7,000, most preferably 2,800 to 4,000. Said molecular weights are as measured by gel permeation chromatography against polystyrene standards.

Such molecular weight values correspond to chain lengths derived from the nominal polymerisation esterification of the polyol and the dicarboxylic acid of from about 1 to about 20, more usually from about 1 to about 10, and particularly from about 1 to about 7.5, repeat units (based on a hydroxy/carboxy ended polyol-dicarboxylic acid ester unit). Of course, the number of "repeat units" and molecular weight are average values and may thus be non-integral across a bulk composition.

The extent to which the total available hydroxyl groups in the reaction components used in making the products of the invention are esterified can have a significant effect on the efficiency of the compounds of and used in the present invention as structurants. Generally a minimum of 40%, more usually at least 45% and desirably at least 50% of the total polyol hydroxyl groups will be esterified.

At lower levels of esterification, the proportion of free hydroxyl groups is sufficiently high to significantly reduce the solubility of the oligoesters and thus to have a detrimental effect on the thickening performance of the structurants.

The maximum number of such ester residues will depend on the number of hydroxyl groups in the original polyol. The level of esterification is usually not more than about 90%, for example up to about 80% of the hydroxyl groups in the original polyol. In reckoning the number of hydroxyl groups in the original polyol, any that react to form ethers under the reaction conditions e.g. as in forming sorbitol from sorbitan, are not included. Within these ranges, the proportion of free hydroxyl groups may be used to modulate or moderate the thickening effects of the compounds.

Suitable specific structurants may be selected from the reaction product of suberic acid and sorbitol and arachidic acid at a molar ratio of 1:2:3 respectively; sebacic acid and sorbitol and arachidic acid at a molar ratio of 1:2:3 respectively; dodecanedioic acid and sorbitol and arachidic acid at a molar ratio of 1:2:3 respectively; suberic acid and sorbitol and behenic acid at a molar ratio of 1:2:3 respectively; suberic acid and sorbitol and lignoceric acid at a molar ratio of 1:2:3 respectively; suberic acid and sorbitol and erucic acid at a molar ratio of 1:2:3 respectively; sebacic acid and sorbitol and behenic acid at a molar ratio of 1:2:3 respectively; sebacic acid and sorbitol and lignoceric acid at a molar ratio of 1:2:3 respectively; sebacic acid and sorbitol and erucic acid at a molar ratio of 1:2:3 respectively; dodecanedioic acid and sorbitol and behenic acid at a molar ratio of 1:2:3 respectively; dodecanedioic acid and sorbitol and lignoceric acid at a molar ratio of 1:2:3 respectively; or dodecanedioic acid and sorbitol and erucic acid at a molar ratio of 1:2:3 respectively.

Most preferably, suitable specific structurants may be selected from the reaction product of suberic acid and sorbitol and behenic acid at a molar ratio of 1:2:3 respectively; sebacic acid and sorbitol and behenic acid at a molar ratio of 1:2:3 respectively; or dodecanedioic acid and sorbitol and behenic acid at a molar ratio of 1:2:3 respectively.

The amount of structurant present in the concentrate may preferably be in the range from 0.1 wt. % to 12.0 wt. %. More preferably, in the range from 0.4 wt. % to 8.0 wt. %. Further preferably, in the range from 0.8 wt. % to 5.0 wt. %. Most preferably, in the range from 1.0 wt. % to 4.0 wt. %.

The structurants of the present invention may be made by a generally conventional esterification using a polyol, a dicarboxylic acid (or a reactive derivative) and a monocarboxylic acid (or a reactive derivative) as starting materials.

One method of making the structurants of the present invention comprises a direct one stage route in which all three components (the polyol, the dicarboxylic acid (or reactive derivative) and the monocarboxylic acid (or reactive derivative)) are mixed and reacted together under (trans-)esterification conditions, particularly at elevated temperatures and in the presence of a catalyst.

The reaction conditions will typically involve using reaction temperatures of from 150° C. to 250° C., and particularly 170° C. to 240° C. Where free acids are used as reagents in direct esterification, the reaction may be carried out under atmospheric pressure or under moderate vacuum, e.g. at pressures from 50 mBar to 250 mBar, particularly about 100 mBar gauge, to facilitate removal of water of reaction. Trans-esterification reactions using lower alkyl esters will usually be carried out at ambient pressure.

Suitable catalysts will depend on the actual starting materials and the desired product. For direct esterification, typical catalysts may include basic catalysts such as alkali metal hydroxides or carbonates, for example sodium or potassium hydroxide or carbonate, particularly potassium carbonate. Typical catalysts may include acidic catalysts, such as sulphonic acids, for example p-toluene sulphonic acid, or phosphorus oxyacids, for example phosphoric acid If it is desirable to avoid colour forming oxidation reactions, especially with starting polyols such as sorbitol, phosphorous acid and catalysts combining phosphoric and/or phosphorous acid with alkali, typically at a molar ratio of from 1:1 to 1:3 may be used. Alternatively, for trans-esterification typical catalysts include relatively mild alkali metal base such as carbonates, particularly potassium carbonate, or titanate esters, such as tetrabutyl titanate, may be used.

The amount of catalyst used will be chosen to achieve the desired level of catalysis and will usually be within the range from 0.5 wt. % to 20 wt. % based on the weight of polyol used. Typically, the amount of catalyst will be in the range from 0.75 wt. % to 10 wt. % based on the polyol.

Higher level of esterification catalyst, for example up to 20 wt. % and particularly about 15 wt. %, may be used to increase preference for the desired reaction to avoid side reactions such as cyclising etherification when using highly hydroxylic polyols like sorbitol. Catalytic materials that promote cyclisation, such as acids, will generally be avoided.

Hydroxyl values (OH) were measured using a method based upon BS 684 Section 2.9 (1976) and results are quoted in $mg(KOH) \cdot g^{-1}$. The hydroxyl value is the amount of base (milligrams KOH) required to neutralise the acid used to acetylate the OH groups in 1 g of sample.

Free acid in the sample increases the consumption of KOH in titration to give falsely low hydroxyl values, so the values are corrected for the contribution of acid OH groups. As directly measured the hydroxyl value includes both hydroxylic and carboxylic OH groups. Therefore, the contribution from hydroxylic OH groups can be obtained by subtracting the acid value from the hydroxyl value to give a value which can be described as the free hydroxyl value.

The hydroxyl value of the structurant of the present invention may be in the range from 15 $mg(KOH) \cdot g^{-1}$ to 250 $mg(KOH) \cdot g^{-1}$. Preferably, in the range from 30 $mg(KOH) \cdot g^{-1}$ to 200 $mg(KOH) \cdot g^{-1}$. More preferably, in the range from 40 $mg(KOH) \cdot g^{-1}$ to 150 $mg(KOH) \cdot g^{-1}$.

The higher values may be achieved by deliberately using a highly hydroxylic polyol, such as sorbitol, as starting material, and carrying out the synthesis so as to minimise loss of free hydroxyl groups, for example avoiding cyclising etherification synthetic side reactions by using non-acid catalysts at relatively high levels.

To determine acid values, a test sample dissolved in a suitable solvent (usually ethanol) is titrated against standard (usually ethanolic) KOH solution with phenophthalein indicator. The acid value was measured using the A.O.C.S. Official method Te 1a-64 (Reapproved 1997), and expressed as the number of milligrams of potassium hydroxide required to neutralise the free fatty acids in 1 g of sample. The results are quoted as "Acid Value" in $mg(KOH) \cdot g^{-1}$.

The acid value of the structurants of the present invention may be less than 25 $mg(KOH) \cdot g^{-1}$. Preferably, less than 20 $mg(KOH) \cdot g^{-1}$. More preferably, less than 12 $mg(KOH) \cdot g^{-1}$. Further preferably, less than 8 $mg(KOH) \cdot g^{-1}$. Most preferably, less than 5 $mg(KOH) \cdot g^{-1}$.

Structurants of the invention may be solids with melting points in the range from 50° C. to 100° C. Preferably, in the range from 60° C. to 85° C.

The surfactant adjuvant of the concentrate will be understood to preferably form the continuous phase of the concentrate. The surfactant adjuvant is preferably a liquid at room temperature and pressure.

The surfactant adjuvant will be understood to serve as an adjuvant for the agrochemical active in the concentrate and/or formulation. The adjuvant would provide adjuvancy to the agrochemical concentrate and/or formulation in which it is comprised.

As used herein, the term 'adjuvant' or 'adjuvancy' refers to compounds which when added to an agrochemical formulation will improve the agrochemical's desired effect. The surfactant adjuvant may affect the diluent, the mixture, the active, or the target by its improvements of the active's performance. The surfactant adjuvant may therefore be used to;

adhere the pesticide on the area where the pesticide is functional;
change the epidermal layer of the leaf surface permitting pesticide entry; and/or
attract the target pest to the pesticide as when used as a food for the pest in baits.

Specific adjuvancy effects may include surfactants, oils, compatibility agents, buffering and conditioning agents, defoaming agents, deposition agents, drift control agents, thickeners, spreaders (wetters), stickers (builders and extenders), emulsifiers (dispersants and suspending agents), plant penetrants, translocators, emulsifiable oils, compatibility agents, buffers, inverting agents, soil penetrants, and/or stabilising agents (UV filters).

The specific nature of the surfactant adjuvant is not critical to the invention and those skilled in the art will be able to select suitable adjuvant systems to optimise the bio-performance of the active ingredient concerned.

The surfactant adjuvant may be selected from a non-ionic surfactant and/or anionic surfactant.

Suitable non-ionic surfactants may be selected from polyethylene oxide-polypropylene oxide block copolymers, polyethylene glycol ethers of linear alcohols, reaction products of fatty acids with ethylene oxide and/or propylene oxide, polyvinyl alcohol, polyvinylpyrrolidone, copolymers of polyvinyl alcohol and polyvinylpyrrolidone, copolymers of (meth)acrylic acid and (meth)-acrylic acid esters, alkyl ethoxylates and alkylaryl ethoxylates which can be optionally phosphated and optionally neutralised with bases, alkanol alkoxylates, and polyoxyalkylenamine derivatives.

Suitable anionic surfactants may be selected from alkali metal and alkaline earth metal salts of alkyl sulphonic acids or alkyl arylsulphonic acids, salts of poly-styrenesulphonic acids, salts of polyvinylsulphonic acids, salts of naphthalene-sulphonic acid-formaldehyde condensation products, salts of condensation products of naphthalenesulphonic acid, and phenolsulphonic acid and formaldehyde, and salts of lignosulphonic acid.

A wide range of adjuvant types is available to those skilled in the art and whilst it is not intended to supply a comprehensive list, typically the adjuvant system may for example comprise one or more enhancers such as ethylene oxide/propylene oxide block copolymers, alcohol ethoxylates (such as Brij 010 and Brij 02), alkyl polysaccharides (such as Atplus 435 or AL2575), polyethoxylated alcohols/fatty alcohols (such as Synperonic A7, Etocas 35), alkyl phenyl ethoxylates (such as Agral 90), polyethoxylated nonyl phenyl ether carboxylic acid (such as Sandopan MA-18), tallow amine ethoxylates, oil based derivatives (either mineral or vegetable) (such as Atplus 411F and Atplus 463), sorbitol, ethoxylated Sorbitan derivatives (such as one of the Tween series of surfactants such as Tween 20, or Arlatone TV), acetylenic diol derivatives (such as one of the Surfynol series), esters of alkoxylated diethylethanolamine (such as Atlox 4915), and polyethyleneglycol. The bioperformance may additionally be enhanced by the inclusion in the formulation of one or more wetting agents such as short chain alcohol ethoxylates.

Preferably, said adjuvant may be selected from ethoxylated sorbitol/sorbitan derivatives or polyethoxylated alcohols/fatty alcohols.

Specifically preferred adjuvants may be selected from polyoxyethylene (7) C12-C15 alcohol (Synperonic A7), C8-C10 alkylpolysaccharide (AL2575), polyoxyethylene (35) castor oil (Etocas 35), polyoxyethylene (12) di-ethyl ethanol amine mono-trimerate (Atlox 4915), polyoxyethylene (40) sorbitol oleate (Arlatone TV), or polyoxyethylene (20) sorbitan mono laurate (Tween 20).

In order to achieve maximum enhancement of the activity of the active ingredient, it may be desired that the surfactant adjuvant concentration is greater than about 50 wt. % of the total concentrate.

The amount of surfactant adjuvant present in the concentrate may preferably at least 50 wt. %. More preferably, at least 65 wt. %. Further preferably, at least 70 wt. %. Even further preferably, at least 80 wt. %. Particularly, at least 90 wt. %. Most preferably, the amount of surfactant adjuvant present in the concentrate is at least 95 wt. %.

The agrochemical active may preferably be a solid phase agrochemical active. Solid agrochemical active compounds are to be understood in the present composition as meaning all substances customary for plant treatment, whose melting point is above 20° C. (standard pressure). Solid agrochemical actives will also include insoluble active ingredients, i.e. active ingredients whose solubility in water is such that a significant solid content exists in the concentrate after addition.

Agrochemical actives refer to biocides which, in the context of the present invention, are plant protection agents, more particular chemical substances capable of killing different forms of living organisms used in fields such as medicine, agriculture, forestry, and mosquito control. Also counted under the group of biocides are so-called plant growth regulators.

Biocides for use in agrochemical formulations of the present invention are typically divided into two sub-groups:
pesticides, including fungicides, herbicides, insecticides, algicides, moluscicides, miticides and rodenticides, and
antimicrobials, including germicides, antibiotics, antibacterials, antivirals, antifungals, antiprotozoals and antiparasites.

In particular, biocides selected from insecticides, fungicides, or herbicides may be particularly preferred.

The term 'pesticide' will be understood to refer to any substance or mixture of substances intended for preventing, destroying, repelling, or mitigating any pest. A pesticide may be a chemical substance or biological agent (such as a virus or bacteria) used against pests including insects, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given.

A fungicide is a chemical control of fungi. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies.

Examples for suitable fungicides, according to the present invention, encompass the following species: (3-ethoxypropyl)mercury bromide, 2-methoxyethylmercury chloride, 2-phenylphenol, 8-hydroxyquinoline sulphate, 8-phenylmercuri oxyquinoline, acibenzolar, acylamino acid fungicides, acypetacs, aldimorph, aliphatic nitrogen fungicides, allyl alcohol, amide fungicides, ampropylfos, anilazine, anilide fungicides, antibiotic fungicides, aromatic fungicides, aureofungin, azaconazole, azithiram, azoxystrobin, barium polysulphide, benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, blasticidin-S, Bordeaux mixture, boscalid, bridged diphenyl fungicides, bromuconazole, bupirimate, Burgundy mixture, buthiobate, butylamine, calcium polysulphide, captafol, captan, carbamate fungicides, carbamorph, carbanilate fungicides, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper (II) carbonate, basic, copper fungicides, copper hydroxide, copper naphthenate, copper oleate, copper oxychloride, copper(II) sulphate, copper sulphate, basic, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dicarboximide fungicides, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, dinitrophenol fungicides, dinobuton, dinocap, dinocton, dinopenton, dinosulphon, dinoterbon, diphenylamine, dipyrithione, disulphiram, ditalimfos, dithianon, dithiocarbamate fungicides, DNOC, dodemorph, dodicin, dodine, DONATODINE, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulph, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, fludioxonil, flumetover, fluopicolide, fluoroimide, fluotrimazole, fluoxastrobin, fluquinconazole, flusilazole, flusulphamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isoprothiolane, isovaledione, kasugamycin, kresoxim-methyl, lime sulphur, mancopper, mancozeb, maneb, mebenil, mecarbinzid, mepanipyrim, mepronil, mercuric chloride, mercuric oxide, mercurous chloride, mercury fungicides, metalaxyl, metalaxyl-M, metam, metazoxolon, metconazole, methasulphocarb, methfuroxam, methyl bromide, methyl isothiocyanate, methylmercury benzoate, methylmercury dicyandiamide, methylmercury pentachlorophenoxide, metiram, metominostrobin, metrafenone, metsulphovax, milneb, morpholine fungicides, myclobutanil, myclozolin, N-(ethylmercury)-p-toluenesulphonanilide, nabam, natamycin, nitrostyrene, nitrothal-isopropyl, nuarimol, OCH, octhilinone, ofurace, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulphamide fungicides, phosdiphen, phthalide, phthalimide fungicides, picoxystrobin, piperalin, polycarbamate, polymeric dithiocarbamate fungicides, polyoxins, polyoxorim, polysulphide fungicides, potassium azide, potassium polysulphide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfiir, pyrrole fungicides, quinacetol, quinazamid, quinconazole, quinoline fungicides, quinone fungicides, quinoxaline fungicides, quinoxyfen, quintozene, rabenzazole, salicylanilide, silthiofam, simeconazole, sodium azide, sodium orthophenylphenoxide, sodium pentachlorophenoxide, sodium polysulphide, spiroxamine, streptomycin, strobilurin fungicides, sulphonanilide fungicides, sulphur, sultropen, TCMTB, tebuconazole, tecloftalam, tecnazene, tecoram, tetraconazole, thiabendazole, thiadifluor, thiazole fungicides, thicyofen, thifluzamide, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, trifloxystrobin, triflumizole, triforine, triticonazole, unclassified fungicides, undecylenic acid, uniconazole, urea fungicides, validamycin, valinamide fungicides, vinclozolin, zarilamid, zinc naphthenate, zineb, ziram, zoxamide, and mixtures thereof.

An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are non-selective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat.

Suitable herbicides may be selected from the group comprising: aryloxycarboxylic acid e.g. MCPA, aryloxyphenoxypropionates e.g. clodinafop, cyclohexanedione oximes e.g. sethoxydim, dinitroanilines e.g. trifluralin, diphenyl ethers e.g. oxyfluorfen, hydroxybenzonitriles e.g. bromoxynil, sulphonylureas e.g. nicosulphuron, triazolopyrimidines e.g. penoxsulam, triketiones e.g. mesotriones, or ureas e.g. diuron.

Particularly preferred herbicides may be selected from 2,4-dichlorophenoxyacetic acid (2,4-D), atrazine, dicamba as benzoic acid, glyphosate, imazapic as imidazolinone, metolachlor as chloroacetamide, picloram, clopyralid, and triclopyr as pyridinecarboxylic acids or synthetic auxins.

An insecticide is a pesticide used against insects in all developmental forms, and includes ovicides and larvicides used against the eggs and larvae of insects. Insecticides are used in agriculture, medicine, industry and the household.

Suitable insecticides may include those selected from:
- Chlorinated insecticides such as, for example, Camphechlor, DDT, Hexachloro-cyclohexane, gamma-Hexachlorocyclohexane, Methoxychlor, Pentachlorophenol, TDE, Aldrin, Chlordane, Chlordecone, Dieldrin, Endosulphan, Endrin, Heptachlor, Mirex and their mixtures;
- Organophosphorous compounds such as, for example, Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulphoton, Ethoprop, Fenamiphos, Fenitrothion, Fenthion, Fosthiazate, Malathion, Methamidophos, Methidathion, Methyl-parathion, Mevinphos, Naled, Omethoate, Oxydemeton-methyl, Parathion, Phorate, Phosalone, Phosmet, Phostebupirim, Pirimiphosmethyl, Profenofos, Terbufos, Tetrachlorvinphos, Tribufos, Trichlorfon and their mixture;
- Carbamates such as, for example, Aldicarb, Carbofuran, Carbaryl, Methomyl, 2-(1-Methylpropyl)phenyl methylcarbamate and their mixtures;
- Pyrethroids such as, for example, Allethrin, Bifenthrin, Deltamethrin, Permethrin, Resmethrin, Sumithrin, Tetramethrin, Tralomethrin, Transfluthrin and their mixtures;
- Plant toxin derived compounds such as, for example, Derris (rotenone), Pyrethrum, Neem (Azadirachtin), Nicotine, Caffeine and their mixtures.
- Neonicotinoids such as imidacloprid.
- Abamectin e.g. emamactin
- Oxadiazines such as indoxacarb
- Anthranilic diamides such as rynaxypyr Rodenticides are a category of pest control chemicals intended to kill rodents. Suitable rodenticides may include anticoagulants, metal phosphides, phosphides, and calciferols (vitamins D), and derivatives thereof.

Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulphate. A nematicide is a type of chemical pesticide used to kill parasitic nematodes (a phylum of worm).

In the following examples, antimicrobials suitable for agrochemical compositions according to the present invention are given.

Bactericidal disinfectants may include those selected from active chlorines, active oxygen, iodine, concentrated alcohols, phenolic substances, cationic surfactants, strong oxidisers, heavy metals and their salts, and concentrated strong acids and alkalis between pH of from 1 to 13. Suitable antiseptics (i.e., germicide agents that can be used on human or animal body, skin, mucoses, wounds and the like) may include diluted chlorine preparations, iodine preparations, peroxides, alcohols with or without antiseptic additives, weak organic acids, phenolic compounds, and cation-active compounds.

Preferred actives are those with systemic or partially systemic mode of action.

Particular preference is given to active compounds from the classes of the azole fungicides (azaconazole, bitertanol, bromuconazole, cyproconazole, diclobutrazole, difenoconazole, diniconazole, diniconazole-M, epoxiconazole, etaconazole, fenarimol, fenbuconazole, fluquinconazole, flurprimidol, flusilazole, flutriafol, furconazole, furconazole-cis, hexaconazole, imazalil, imazalil sulphate, imibenconazole, ipconazole, metconazole, myclobutanil, nuarimol, oxpoconazole, paclobutrazole, penconazole, pefurazoate, prochloraz, propiconazole, prothioconazole, pyrifenox, simeconazole, tebuconazole, tetraconazole, triadimefon, triadimenol, triflumizole, triforin, triticonazole, uniconazole, voriconazole, viniconazole), strobilurin fungicides (azoxystrobin, dimoxystrobin, fluoxastrobin, kresoxim-methyl, metominostrobin, orysastrobin, picoxystrobin, pyraclostrobin, trifloxystrobin), the SDH fungicides, the chloronicotinyl insecticides (clothianidin, dinotefuran, imidacloprid, thiamethoxam, nitenpyram, nithiazin, acetamiprid, nitenpyram, thiacloprid), the insecticidal ketoenols (spirodiclofen, spiromesifen, spirotetramate), fiproles (fiprole, ethiprole) and butenolides, and also pymetrozine, fluopicolid, N-(3',4'-dichloro-5-fluoro-1,1'-biphenyl-2-yl)-3-(difluoromethyl)-1-methyl-1H-pyrazole-4-carboxamide and N-{2-[3-chloro-5-(trifluoromethyl)-2-pyridinyl]ethyl}-2-(trifluoromethyl)benzamide. Particular preference is also given to herbicides, in particular sulphonylureas, triketones and herbicidal ketoenols, and also safeners.

The structurant of the present invention may be applied to a wide range of insoluble active ingredients (that is to say active ingredients whose solubility in water is such that a significant solid content exists in the concentrate). It is especially applicable to suspension concentrates which either contain a high loading of adjuvant, involve an active ingredient which requires formulation at low pH, or both.

Preferred examples of such agrochemical actives may be selected from;
- the fungicides tebuconazole, prothioconazole, N-(3',4'-dichloro-5-fluoro-1,1'-biphenyl-2-yl)-3-(difluoromethyl)-1-methyl-1H-pyrazole-4-carboxamide (known from WO 03/070705), N-{2-[3-chloro-5-(trifluoromethyl)-2-pyridinyl]ethyl}-2-(trifluoromethyl)benzamide (known from WO 04/16088), trifloxystrobin, fluopicolid, azoxystrobin;
- the insecticides imidacloprid, thiamethoxam, clothianidin, thiacloprid, spirotetramate, fipronil, ethiprol, carbaryl, cypermethrin;
- the herbicides thiencarbazone, sulcotrione, mesotrione, tembotrione, pyrasulphotole, iodosulphuron, mesosulphuron, forarnsulphuron, nicosulfuron, and pyrazosulfuron-ethyl.

Particularly preferred examples of agrochemical actives may be selected from mesotrione or sulcotrione. When the active ingredient is mesotrione or sulcotrione, the concentrate of the invention is particularly suitably for use as an herbicide.

The concentration of the agrochemical active in the concentrate is not critical for the purposes of the present invention, and may be determined by other factors as required. The concentration of the agrochemical active is preferably in the range from 50 g/l to 500 g/l. More preferably, in the range from 75 g/l to 250 g/l. Most preferably, in the range from 90 g/l to 180 g/l.

In an alternative embodiment the concentrate may optionally comprising nutrients in addition to, or as an alternative to, pesticide actives. In such formulations the nutrient is typically in a dry form.

Nutrients refer to chemical elements and compounds which are desired or necessary to promote or improve plant growth. Suitable nutrients generally are described as macronutrients or micronutrients. Suitable nutrients for use in the concentrates according to the invention are all nutrient compounds, preferably those which are solid at room temperature.

Micronutrients typically refer to trace metals or trace elements, and are often applied in lower doses. Suitable micronutrients include trace elements selected from zinc, boron, chlorine, copper, iron, molybdenum, and manganese. The micronutrients may be in a soluble form or included as insoluble solids, and may be salts or chelated.

Macronutrients typically refer to those comprising nitrogen, phosphorus, and potassium, and include fertilisers such as ammonium sulphate, and water conditioning agents. Suitable macro nutrients include fertilisers and other nitrogen, phosphorus, potassium, calcium, magnesium, sulphur containing compounds, and water conditioning agents.

Suitable fertilisers include inorganic fertilisers that provide nutrients such as nitrogen, phosphorus, potassium or sulphur. Fertilisers may be included in diluted formulations at relatively low concentrations or as more concentrated solutions, which at very high levels may include solid fertiliser as well as solution.

It is envisaged that inclusion of the nutrient would be dependent upon the specific nutrient, and that micronutrients would typically be included at lower concentrations whilst macronutrients would typically be included at higher concentrations.

When present, the proportion of nutrient in the total concentrate is typically from 5 wt. % to 40 wt. %, more usually, 10 wt. % to 35 wt. %, particularly 15 wt. % to 30% wt. %.

Agrochemical concentrates are agrochemical compositions, which may be aqueous or non-aqueous, and which are designed to be diluted with water (or a water based liquid) to form the corresponding end-use agrochemical formulations, typically spray formulations. Said concentrates include those in liquid form (such as solutions, emulsions, or dispersions) and in solid form (especially in water dispersible solid form) such as granules or powders.

Accordingly, the concentrate of the present invention may be formulated as an emulsion concentrate (EW), suspension concentrate (SC), as an oil-based suspension concentrate (OD), and/or suspoemulsions (SE). In an OD, SC, or SE formulations the active compound may be present as a solid or emulsified liquid. It is envisaged that the structurant of the present invention will particularly find use in a SC, OD, or SE formulation. In particular, the structurant of the present invention may particularly find use in a SC formulation.

It will be appreciated that typically SC formulations are water based, but that the concentrates of the present invention are described as having low or no water. Therefore, the preferred concentrates of the present invention may be thought of as being SC-like or a non-water based SC where the continuous phase is instead formed by the surfactant adjuvant.

It is typically known that the higher the surfactant adjuvant concentration in the concentrate in order to provide the desired bio-performance enhancement, the more difficult it becomes to achieve a stable SC. The benefits of the present invention are therefore most apparent at higher adjuvant concentrations where stable suspension concentrates can be achieved at high concentrations of adjuvant as a result of the structurant.

The concentrate may be preferably substantially non-aqueous. Preferably, the continuous phase is at least 50 wt. % non-aqueous. More preferably, at least 65 wt. %. Further preferably, at least 70 wt. %. Even further preferably, at least 80 wt. %. Particularly preferably, at least 90 wt. %. Most preferably, at least 95 wt. %.

The continuous phase may be substantially or entirely non-aqueous. It will be understood that the amount of water present in the concentrate may preferably be less than 50 wt. %. More preferably, less than 35 wt. %. Further preferably, less than 30 wt. %. Even further preferably, less than 20 wt. %. Particularly, less than 10 wt. %. Most preferably, the amount of water present in the concentrate is less than 5 wt. %.

The amount of surfactant adjuvant and other components may be present in the concentrate such that the concentrate does not comprise any added water, although some trace amounts of water may be present in any of the components.

The structurant of the present invention will typically be used in an amount proportional to the amount of the surfactant adjuvant in the concentrate. The ratio of structurant to surfactant adjuvant in the concentrate is preferably at a weight ratio of from about 1:20 to about 1:100. More preferably, from about 1:50 to about 1:90. This ratio range will generally be maintained for concentrates and in the agrochemical spray formulations.

The structurants of the present invention provide for desired stability of the resulting concentrates. The concentrates do not undergo separation under storage. Additionally, the concentrates return to being homogeneous liquids at room temperature after being frozen.

It has been found that the structuring of the SC of the present invention provides excellent stability over time and at various temperatures, and even when the SC undergoes shear forces for example on mixing.

The concentrates of the present invention, in particular when SCs, have a maximum separation of 15% and preferably not more than 8% at an accelerated test over 28 days at 54° C. where the separation is as defined in the Examples. Most preferably, the concentrate has no more than 2% separation of an accelerated test over 28 days at 54° C.

The concentrates of the present invention, have a decrease in viscosity when not under between 24 hours and 14 days of no more than 30%, preferably no more than 20%, most preferably no more than 15%.

The concentrates of the present invention, have a decrease in viscosity under low shear between 24 hours and 14 days of no more than 30%, preferably no more than 20%, most preferably no more than 15%.

The concentrates of the present invention, have an increase in D(0.5) particle size of no more than 5% between 24 hours and 14 days at 54° C. Preferably, the concentrate has no increase in particle size.

The concentrates of the present invention, have an increase in D(0.9) particle size of no more than 5% between 24 hours and 14 days at 54° C. Preferably, the concentrate has no increase in particle size.

The concentrates of the present invention, have a suspensibility of at least 60% at 24 hours, where the suspensibility is as defined in the Examples. Preferably, at least 70%. Most preferably, at least 80%.

The concentrates of the present invention, have a variation in pH of no more than 20% when at 54° C. between 24 hours and 28 days. Preferably, no more than 10%. Most preferably, no more than 5%.

Agrochemically active compounds require a formulation which allows the active compounds to be taken up by the plant/the target organisms. When concentrates (solid or liquid) are used as the source of active agrochemical and/or adjuvant, the concentrates will typically be diluted to form end-use formulations, typically spray formulations. The dilution may be with water at from 1 to 10,000, particularly 10 to 1,000, times the total weight of the concentrate to form the spray formulation.

Said concentrates may be diluted for use resulting in a dilute composition having an agrochemical active concentration of about 0.5 wt. % to about 1 wt. %. In said dilute composition (for example, a spray formulation, where a spray application rate may be from 10 to 500 $l \cdot ha^{-1}$) the agrochemical active concentration may be in the range from about 0.001 wt. % to about 1 wt. % of the total formulation as sprayed.

Spray formulations are aqueous agrochemical formulations including all the components which it is desired to apply to the plants or their environment. Spray formulations can be made up by simple dilution of concentrates containing desired components (other than water), or by mixing of the individual components, or a combination of diluting a concentrate and adding further individual components or mixtures of components. Typically such end use mixing is carried out in the tank from which the formulation is sprayed, or alternatively in a holding tank for filling the spray tank. Such mixing and mixtures are typically termed tank mixing and tank mixtures.

Where the agrochemical active is present in the aqueous end use formulation as solid particles, most usually it will be present as particles mainly of active agrochemical. However, if desired, the active agrochemical can be supported on a solid carrier e.g. silica or diatomaceous earth, which can be a solid support, filler or diluent material.

The spray formulations will typically have a pH within the range from moderately acidic (e.g. about 3) to moderately alkaline (e.g. about 10), and particular near neutral (e.g. about 5 to 8). More concentrated formulations will have similar degrees of acidity/alkalinity, but as they may be largely non-aqueous, pH is not necessarily an appropriate measure of this.

The agrochemical formulation may include solvents (other than water) such as monopropylene glycol, oils which can be vegetable or mineral oils such as spray oils. Such solvents may be included as a solvent for the surfactant adjuvant, and/or as a humectant, e.g. especially propylene glycol. When used such solvents will typically be included in an amount of from 5 wt. % to 500 wt. %, desirably 10 wt. % to 100 wt. %, by weight of the surfactant adjuvant. Such combinations can also include salts such as ammonium chloride and/or sodium benzoate, and/or urea especially as gel inhibition aids.

The concentrate and/or agrochemical formulation may also include other components as desired. These other components may be selected from those including:
  binders, particularly binders which are readily water soluble to give low viscosity solutions at high binder concentrations, such as polyvinylpyrrolidone; polyvinyl alcohol; carboxymethyl cellulose; gum arabic; sugars e.g. sucrose or sorbitol; starch; ethylene-vinyl acetate copolymers, sucrose and alginates,
  diluents, absorbents or carriers such as carbon black; talc; diatomaceous earth; kaolin; aluminium, calcium or magnesium stearate; sodium tripolyphosphate; sodium tetraborate; sodium sulphate; sodium, aluminium and mixed sodium-aluminium silicates; and sodium benzoate,
  disintegration agents, such as surfactants, materials that swell in water, for example carboxy methylcellulose, collodion, polyvinylpyrrolidone and microcrystalline cellulose swelling agents; salts such as sodium or potassium acetate, sodium carbonate, bicarbonate or sesquicarbonate, ammonium sulphate and dipotassium hydrogen phosphate;
  wetting agents such as alcohol ethoxylate and alcohol ethoxylate/propoxylate wetting agents;
  dispersants such as sulphonated naphthalene formaldehyde condensates and acrylic copolymers such as the comb copolymer having capped polyethylene glycol side chains on a polyacrylic backbone;
  emulsifiers such as alcohol ethoxylates, ABA block co polymers, or castor oil ethoxylates;
  antifoam agents, e.g. polysiloxane antifoam agents, typically in amounts of 0.005 wt. % to 10 wt. % of the formulation;
  viscosity modifiers such as commercially available water soluble or miscible gums, e.g. xanthan gums, and/or cellulosics, e.g. carboxy-methyl, ethyl or propylcellulose; and/or
  preservatives and/or anti-microbials such as organic acids, or their esters or salts such as ascorbic e.g. ascorbyl palmitate, sorbic e.g. potassium sorbate, benzoic e.g. benzoic acid and methyl and propyl 4-hydroxybenzoate, propionic e.g. sodium propionate, phenol e.g. sodium 2-phenylphenate; 1,2-benzisothiazolin-3-one; or formaldehyde as such or as paraformaldehyde; or inorganic materials such as sulphurous acid and its salts, typically in amounts of 0.01 wt. % to 1 wt. % of the formulation.

The invention further includes a method of treating plants using agrochemical formulations including at least one agrochemical active, surfactant adjuvant, and structurant. These may formed by dilution of the concentrate of the first aspect.

Accordingly the invention further includes methods of use including:
  a method of killing or inhibiting vegetation by applying to the vegetation, or the immediate environment of the vegetation e.g. the soil around the vegetation, a spray formulation including at least one dispersed phase agrochemical, the surfactant adjuvant, and the structurant of the first aspect; and/or
  a method of killing or inhibiting pests of plants by applying to the plants or the immediate environment of the plants e.g. the soil around the plants, a spray formulations including at least one dispersed phase agrochemical which is one or more pesticides, for example insecticides, fungicides or acaricides, the surfactant adjuvant, and the structurant of the first aspect.

All of the features described herein may be combined with any of the above aspects, in any combination.

In order that the present invention may be more readily understood, reference will now be made, by way of example, to the following description.

It will be understood that all tests and physical properties listed have been determined at atmospheric pressure and room temperature (i.e. 25° C.), unless otherwise stated herein, or unless otherwise stated in the referenced test methods and procedures.

The following test methods were used to determine performance of the adjuvant compositions.

Stability—The stability of all the formulations was assessed after the stated time period at room temperature (RT) and 54° C. The samples were tested in a Turbiscan to measure any sedimentation/creaming that may have occurred.

Viscosity—Samples were tested on a TA Instruments DHR-3 rheometer. The rheometer was used to assess their stability over the stated time period. This was done measuring the viscosity profiles and the changes in the samples structure and behaviour over the stated time period. Two tests were carried out to achieve this, a flow test and an oscillation test.
 i. Flow test—measured the sample viscosity over a range of torques (force) and was used to look at the storage viscosity and application viscosity of a formulation. As the samples were shear thinning (viscosity decreases with increasing torque), the range over which they shear thin provides information on how homogeneous the samples structure was.
 ii. Oscillation test—involved applying an oscillating torque to the sample to measure how solid and liquid the sample and which behaviour dominates. Also used to look at the samples LVER (linear visco-elastic region). The length of this region provides information on the particle size distribution of the sample which would indicate how well the formulations active is dispersed. All testing was carried out at 20° C.

Suspensibility (CIPAC MT161 SOP 0039)—Sample was diluted in 342 ppm hard water with 5 ml of concentrate and 95 ml of water. 40 ml of 342 ppm $Ca^{2+}$ water was placed in 100 ml stoppered measuring cylinder. 5 ml of the formulation was added and topped up to 100 ml mark with 342 $Ca^{2+}$ ppm water (mimicking a 20 fold dilution upon application). The sample was inverted 30 times and left to stand for 30 minutes. The top 90% of the suspension was removed by using a vacuum pump connected to a catch pot. The 90% was then dried to constant weight at 50° C. overnight in an evaporating dish. The suspensibility was calculated using the weight of the solid material obtained.

Particle size values—the D(v,0.5) and D(v,0.9) values were determined by dynamic light scattering analysis using a Malvern Mastersizer 2000 with a Hydro 2000SM attachment running on water set at 2,100 rpm. The refractive index of the material was set as 1.53 with an absorbance of 0.1. 12,000 snaps were taken over 12 seconds to obtain the data. An average of three runs was used to determine a final particle size. From the particle size values obtained, D(v,0.5) and D(v,0.9) values were readily determined.

Example Synthesis of Structurant (S1)

Anhydrous sorbitol (32.76 g, 0.18 mol), sebacic acid (18.18 g, 0.09 mol), behenic acid (91.80 g, 0.27 mol), and potassium carbonate (catalyst) (1.86 g, 7.5 mol. % based on the amount of polyol) were charged to a 250 ml round bottomed flask fitted with a propeller stirrer, side-arm water condenser, collection flask, nitrogen sparge, thermometer (thermocouple), and isomantle. The mixture was heated with stirring (300 rpm) to 170° C. under nitrogen sparge and at a vacuum of 100 mbar (gauge) removing water of reaction through the condenser. The reaction was monitored by acid value, and stopped when this fell below 20 (after 4 to 5 hrs) and the product discharged. The measured molecular weight was Mn 1480 and Mw 3220.

Example Formulations with Various Surfactant Adjuvants

A number of concentrates were formed using the structurant S1 synthesised above. Each concentrate comprised the selected amount of structurant with the rest of the concentrate being the respective surfactant adjuvant. The resultant blend was then heated to 80-85° C. and stirred at about 500 rpm until a homogenous liquid was obtained. Samples were then left to cool. The concentrates made are listed in Table 1.

TABLE 1

Concentrates Formed

| Example | Surfactant Adjuvant | | Amount of S1 (wt. %) |
|---|---|---|---|
| | Trade Name | Chemical Name | |
| C1 | Synperonic A7 | Polyoxyethylene (7) C12-C15 alcohol | 3.0 |
| C2 | AL 2575 | C8-C10 Alkylpolysaccharide | 4.0 |
| C3 | Etocas 35 | Polyoxyethylene (35) castor oil | 2.0 |
| C4 | Atlox 4915 | Polyoxyethylene (12) Di-ethyl ethanol amine mono-trimerate | 2.0 |
| C5 | Arlatone TV | Polyoxyethylene (40) sorbitol oleate | 2.0 |
| C6 | Tween 20 | Polyoxyethylene (20) sorbitan mono laurate | 2.5 |

To assess there long term compatibility the samples were stored at 54° C. for 28 days and changes in appearance and rheology were assessed.

Viscosity

The viscosity was measured for C1-C3, C5, and C6 after 24 hours and 28 days, and at different torque values. The results are listed in Table 2.

TABLE 2

Viscosity of Concentrates

| | Viscosity after 24 hours (Pa · s) | | Viscosity after 28 days (Pa · s) | |
|---|---|---|---|---|
| Example | At Low torque of 0 μNm | At Torque of 5 μNm | At Low torque of 0 μNm | At Torque of 5 μNm |
| C1 | 15482 | 14328 | 12613 | 10589 |
| C2 | 4217 | 3874 | 3764 | 3005 |
| C3 | 1428 | 1274 | 1320 | 1250 |
| C5 | 2458 | 2257 | 1972 | 1614 |
| C6 | 15241 | 15821 | 14817 | 16993 |

The results show that the viscosities of all of the concentrates C1-C3, C5, and C6 remain relatively constant from an initial point at 24 hours to 28 days. This also remains the case even when placed under some shear.

Stability

The stability with regard to separation for concentrates C1-C6 was tested visually at both room temperature and elevated temperature. Table 3 shows the visual observations for the concentrates C1-C6 over 28 days.

TABLE 3

Visual Stability Observations

| Sample | 24 hours | | 7 days | | 28 days | |
|---|---|---|---|---|---|---|
| | RT | 54° C. | RT | 54° C. | RT | 54° C. |
| C1 | NS | NS | NS | NS | NS | NS |
| C2 | NS | NS | NS | NS | NS | NS |
| C3 | NS | NS | NS | NS | NS | NS |
| C4 | NS | NS | NS | NS | NS | NS |
| C5 | NS | NS | NS | NS | NS | NS |
| C6 | NS | NS | NS | NS | NS | NS |

NS—signifies no separation
RT—room temperature

All the samples did not appear to be visually impacted either at room temperature or at elevated temperature over the 28 day period. None of the concentrates C1-C6 showed signs of the structurant S1 precipitating out.

It should be noted that testing at elevated temperature was performed as it is generally understood to represent an accelerated way of assessing room temperature properties over time. For example, a concentrate kept at 54° C. for 14 days is understood to provide similar results compared to keeping a concentrate at room temperature for two years.

As a result of the stability and viscosity tests it can be seen that the structurant S1 was shown to produce stable surfactant adjuvant formulations with a number of surfactants covering a broad range of chemistries, including examples of alkylpolysaccharides, castor oil ethoxylates, and ethoxylated triglyceride esters. Structurant S1 was been shown to successfully structure all the surfactants tested.

Example Formulations with Active

Concentrates were formed including the herbicide mesotrione, a surfactant adjuvant (polyoxyethylene (20) sorbitan mono laurate), and structurant S1. The mesotrione (from Helm AG) had an assay of 98%, and specific gravity of 1.47 g/cm$^3$.

To form the concentrates, the surfactant adjuvant, water (if applicable), and structurant S1 were combined and heated to 80-85° C. with stirring until all solid had melted. When the mixture had cooled the active and any other components were added and stirred together at around 500 rpm. The resultant mixture was then milled at around 3,500 rpm using an Eiger Torrance mini motor mill. The concentrates were pH adjusted using 0.1M phosphoric acid to approximately pH 2.5 to satisfy the mesotrione requirement. The formulations of the active containing concentrates are shown in Table 4.

TABLE 4

Concentrates with Mesotrione

| Component | C7 (wt. %) | C8 (wt. %) |
|---|---|---|
| Mesotrione | 15.0 | 9.7 |
| Atlox 4913 | 1.0 | 0.97 |
| Atlas G5002L | 0.5 | 0.48 |
| Tween 20 | 80.5 | 85.85 |
| S1 | 3.0 | 3.0 |
| Water | 0.0 | 0.0 |

Atlox 4913 is an acrylic copolymer dispersant for SCs. Atlas G5002L is polyalkylene glycol ether polymeric emulsifier. Tween 20 is a surfactant adjuvant (polyoxyethylene (20) sorbitan mono laurate). All three components are obtainable from Croda Europe Ltd, UK.

Formulations C7 and C8 contained mesotrione, with a continuous phase of Tween 20, and no additional water.

Stability

The stability with regard to separation for concentrates C7 and C8 was tested visually at room temperature (RT) after 24 hours. Table 5 shows the visual observations for the concentrates C7 and C8.

TABLE 5

Visual Stability Observations

| Sample | 24 hours at RT |
|---|---|
| C7 | no separation |
| C8 | no separation |

Both concentrates C7 and C8 did not appear to be visually impacted at room temperature over the 24 hour period. Neither concentrate showed signs of the structurant S1 precipitating out at 24 hours.

The formulations C7 and C8 were reproduced but with differing levels of S1, and were pH adjusted with phosphoric acid to pH 3.5. These further concentrates are shown in Table 6.

TABLE 6

Further Concentrates with Mesotrione

| Component | C9 (wt. %) | C10 (wt. %) |
|---|---|---|
| Mesotrione | 15.0 | 9.7 |
| Atlox 4913 | 1.0 | 0.97 |
| Atlas G5002L | 0.5 | 0.48 |
| Tween 20 | 81.0 | 86.35 |
| S1 | 2.5 | 2.5 |
| Water | 0.0 | 0.0 |

Again, both concentrates C9 and C10 contained mesotrione, with a continuous phase of Tween 20, and no additional water.

Stability

The stability with regard to separation for the concentrates C9 and C10 was tested visually at both room temperature and elevated temperature. Table 7 shows the visual observations for the concentrates C9 and C10 over 14 days.

TABLE 7

Visual Stability Observations

| Sample | 24 hours | | 7 days | | 14 days | |
|---|---|---|---|---|---|---|
| | RT | 54° C. | RT | 54° C. | RT | 54° C. |
| C9 | NS | NS | NS | 2% St | NS | 2% St |
| C10 | NS | NS | NS | 4% St | NS | 6% St |

NS—signifies no separation
RT—room temperature
St—signifies separation at top (>1 and <20%) oil or water Table 7 shows the visual observation data for the formulations at room temperature and accelerated heat testing.

Both the concentrates C9 and C10 did not appear to be visually impacted at room temperature over a 14 day period. Neither concentrate showed signs of the structurant S1 precipitating out.

At elevated temperature some separation was observed at longer periods of 7 and 14 days, albeit the amount of sedimentation was low.

Suspensibility

The suspensibility of the concentrates C9 and C10 was also tested, with the results shown in Table 8.

TABLE 8

Suspensibility Results

| Formulation | % at 24 hours |
|---|---|
| C9 | 84.7 |
| C10 | 89.9 |

All formulations passed the suspensibility testing giving high percentage results well above the 60% pass mark.

Viscosity

The viscosity of the concentrates C9 and C10 was also tested over a 14 day period, with the results shown in Table 9. The shear rates were 3.4 s$^{-1}$ for 10 rpm, and 34 s$^{-1}$ for 100 rpm.

TABLE 9

Viscosity Results

| Sample | 24 hours 10 rpm (cP) | 24 hours 100 rpm (cP) | 14 days 10 rpm (cP) | 14 days 100 rpm (cP) |
|---|---|---|---|---|
| C9 | 5125 | 950 | 5575 | 1138 |
| C10 | 5875 | 1255 | 4725 | 908 |

Table 8 shows the viscosity data for both concentrates after 24 hours and 14 days. The data shows that when compared to the result at 24 hours, the viscosity after 14 days was virtually the same. This stability in viscosity over time was seen at both low and higher shear.

Particle Size

The particle sizes in each concentrate were also tested at elevated temperature and across a 14 day period. The particle size results are shown in Table 10.

TABLE 10

Particle Size Results

| | 24 hours at 54° C. | | 14 days at 54° C. | |
|---|---|---|---|---|
| Sample | D(0.5) | D(0.9) | D(0.5) | D(0.9) |
| C9 | 8.138 | 37.754 | 5.324 | 24.570 |
| C10 | 6.631 | 31.377 | 6.063 | 23.424 |

Table 10 shows the particle size data for all the formulations over 14 days. Particle size is known to be related to suspensibility. An increase in particle sizes would indicate a decrease in suspensibility. The particle sizes of the concentrates did not show any increase in particle sizes across the 14 day period therefore indicating suspensibility is maintained even at elevated temperature.

pH Testing

The pH was recorded for concentrate C9 and C10 after 24 hours and 28 days for samples held at 54° C. The results are shown in Table 11.

TABLE 11 pH data

| Sample | pH at 24 hours | pH at 28 days |
|---|---|---|
| C9 | 3.51 | 3.54 |
| C10 | 3.44 | 3.49 |

Table 11 shows the pH data for both concentrate C9 and C10 at 24 hours and 28 days. The data shows that none of the formulations underwent any significant shift in pH during the period.

The structurants of the present invention were used successfully to structure several formulations, with stability monitored over 14 days. The structurants provided good rheology performance over time, low or no sedimentation, and little particle size degradation. The concentrates also passed suspensibility testing indicating that the structurants of the present invention do not cause negative effects when the concentrates are diluted with water as they would be prior to normal use.

It is to be understood that the invention is not to be limited to the details of the above embodiments, which are described by way of example only. Many variations are possible.

The invention claimed is:

1. A stable agrochemical concentrate, comprising:
   i) at least one structurant, said structurant being a polyol ester of a $C_4$ to $C_{16}$ dicarboxylic acid;
   ii) a surfactant that constitutes greater than 50 wt. % of the concentrate; and
   iii) at least one agrochemical active in the form of solid particles;
   wherein the polyol ester is an ester of:
   a $C_4$ to $C_{16}$ dicarboxylic acid;
   a $C_2$ to $C_8$ polyol; and
   a $C_{16}$ to $C_{30}$ monocarboxylic fatty acid,
   wherein the concentrate shows no separation after 24 hours at room temperature.

2. The concentrate according to claim 1, wherein the $C_2$ to $C_8$ polyol is selected from the group consisting of ethylene glycol, isosorbide, 1,3-propanediol, trimethylolpropane, glycerol, erythritol, threitol, pentaerythritol, sorbitan, arabitol, xylitol, ribitol, fucitol, mannitol, sorbitol, galactitol, iditol, inositol, and volemitol.

3. The concentrate according to claim 2, wherein the $C_2$ to $C_8$ polyol is sorbitol or sorbitan.

4. The concentrate according to claim 1, wherein the $C_4$ to $C_{16}$ dicarboxylic acid is a linear dicarboxylic acids having terminal carboxyl groups bridged by a $C_6$ to $C_{14}$ alkyl group or a $C_6$ to $C_{14}$ alkenyl group.

5. The concentrate according to claim 4, wherein the $C_4$ to $C_{16}$ dicarboxylic acid is selected from adipic acid (hexanedioic acid), pimelic acid (heptanedioic acid), suberic acid, azelaic acid, sebacic acid (decanedioic acid), undecane dicarboxylic acid, dodecane dicarboxylic acid (dodecanedioic acid), tetradecanedioic acid, hexadecanedioic acid, or combinations thereof.

6. The concentrate according to claim 5, wherein the $C_4$ to $C_{16}$ dicarboxylic acid is selected from suberic acid, sebacic acid, or dodecanedioic acid.

7. The concentrate according to claim 1, wherein the $C_{16}$ to $C_{30}$ monocarboxylic fatty acid is selected from palmitic acid, stearic acid, arachidic acid, behenic acid, lignoceric acid, cerotic acid, or montanic acid.

8. The concentrate according to claim 1, wherein the molar ratio of $C_4$ to $C_{16}$ dicarboxylic acid, $C_2$ to $C_8$ polyol, and $C_{16}$ to $C_{30}$ monocarboxylic fatty acid present in the structurant is in the range from 0.5-1.5:1.5-2.5:2.5-3.5 respectively.

9. The concentrate according to claim 1, wherein the number average molecular weight of the structurant is in the range from 600 to 8,000.

10. The concentrate according to claim 1, wherein the structurant is obtainable from reaction of suberic acid and sorbitol and behenic acid at a molar ratio of 1:2:3 respectively; sebacic acid and sorbitol and behenic acid at a molar ratio of 1:2:3 respectively; or dodecanedioic acid and sorbitol and behenic acid at a molar ratio of 1:2:3 respectively.

11. The concentrate according to claim 1, wherein the amount of structurant present in the concentrate is in the range from 0.1 wt. % to 12.0 wt. %.

12. The concentrate according to claim 1, wherein the surfactant is a liquid, and forms a continuous phase of the concentrate.

13. The concentrate according to claim 1, wherein the surfactant is either:
a non-ionic surfactant selected from polyethylene oxide-polypropylene oxide block copolymers, polyethylene glycol ethers of linear alcohols, reaction products of fatty acids with ethylene oxide and/or propylene oxide, polyvinyl alcohol, polyvinylpyrrolidone, copolymers of polyvinyl alcohol and polyvinylpyrrolidone, copolymers of (meth)acrylic acid and (meth)-acrylic acid esters, alkyl ethoxylates and alkylaryl ethoxylates which can be optionally phosphated and optionally neutralised with bases, alkanol alkoxylates, and polyoxyalkylenamines; or
an anionic surfactant selected from alkali metal and alkaline earth metal salts of alkyl sulphonic acids or alkyl arylsulphonic acids, salts of poly-styrenesulphonic acids, salts of polyvinylsulphonic acids, salts of naphthalene-sulphonic acid-formaldehyde condensation products, salts of condensation products of naphthalenesulphonic acid, and phenolsulphonic acid and formaldehyde, and salts of lignosulphonic acid.

14. The concentrate according to claim 1, wherein the surfactant is selected from polyoxyethylene (7) $C_{12}$-$C_{15}$ alcohol (Synperonic A7), C8-C10 alkylpolysaccharide (AL2575), polyoxyethylene (35) castor oil (Etocas 35), polyoxyethylene (12) di-ethyl ethanol amine mono-trimerate (Atlox 4915), polyoxyethylene (40) sorbitol oleate (Arlatone TV), or polyoxyethylene (20) sorbitan mono laurate (Tween 20).

15. The concentrate according to claim 1, comprising less than 10 wt. % water.

16. The concentrate according to claim 1, wherein the agrochemical active is a solid phase agrochemical active.

17. The concentrate according to claim 1, wherein the concentrate is formulated as a suspension concentrate, oil-based suspension concentrate, or suspoemulsion formulation.

18. The concentrate according to claim 1, wherein the concentrate has a continuous phase that is at least 50 wt. % non-aqueous.

19. The concentrate according to claim 1, wherein the ratio of structurant to surfactant in the concentrate is at a weight ratio of from about 1:20 to about 1:100.

20. The concentrate according to claim 1, which further comprises at least one nutrient.

21. The concentrate according to claim 1, wherein the $C_2$ to $C_8$ polyol is selected from the group consisting of ethylene glycol, isosorbide, 1,3-propanediol, trimethylolpropane, erythritol, threitol, pentaerythritol, sorbitan, arabitol, xylitol, ribitol, fucitol, mannitol, sorbitol, galactitol, iditol, inositol, volemitol, and mixtures of any of these.

22. The concentrate according to claim 21, wherein said ethylene glycol, isosorbide, 1,3-propanediol, trimethylolpropane, erythritol, threitol, pentaerythritol, sorbitan, arabitol, xylitol, ribitol, fucitol, mannitol, sorbitol, galactitol, iditol, inositol, volemitol, or mixtures of these is/are the only polyols included in the polyol ester.

23. An agrochemical formulation formed by dilution of the concentrate in accordance with claim 21.

24. A method of treating vegetation to control pests, the method comprising applying an agrochemical formulation in accordance with claim 23, either to said vegetation or to the immediate environment of said vegetation.

25. A method of preparing a concentrate in accordance with claim 1, said method comprising mixing:
at least one agrochemical active in the form of solid particles;
at least one structurant, said structurant being a polyol ester of a $C_4$ to $C_{16}$ dicarboxylic acid; and
surfactant;
and grinding and/or milling said mixture.

* * * * *